United States Patent [19]

Hernandez

[11] 3,999,548

[45] Dec. 28, 1976

[54] DISPOSABLE DIAPER HAVING FLUID TRAP

[75] Inventor: John Hernandez, East Brunswick, N.J.

[73] Assignee: Colgate-Palmolive Company, New York, N.Y.

[22] Filed: Dec. 29, 1975

[21] Appl. No.: 644,392

[52] U.S. Cl. .............................. 128/284; 128/287
[51] Int. Cl.² .......................................... A61F 13/16
[58] Field of Search .............. 128/284, 287, 290 R, 128/286

[56] References Cited
UNITED STATES PATENTS

| | | | |
|---|---|---|---|
| 2,800,906 | 7/1957 | Hinton | 128/286 |
| 3,386,442 | 6/1968 | Sabee | 128/287 |
| 3,875,943 | 4/1975 | Fischer | 128/287 |
| 3,927,673 | 12/1975 | Taylor | 128/287 |

*Primary Examiner*—Aldrich F. Medbery
*Attorney, Agent, or Firm*—Norman Blumenkopf; Murray M. Grill; Herbert S. Sylvester

[57] ABSTRACT

A disposable diaper comprising a waterproof back sheet, a hydrophobic sheet, and an hydrophilic pad sandwiched between the back sheet and the face sheet. The diaper is folded to define a box pleated configuration. Sealing strips of waterproof material separate from the back sheet are secured to the face sheet.

10 Claims, 12 Drawing Figures

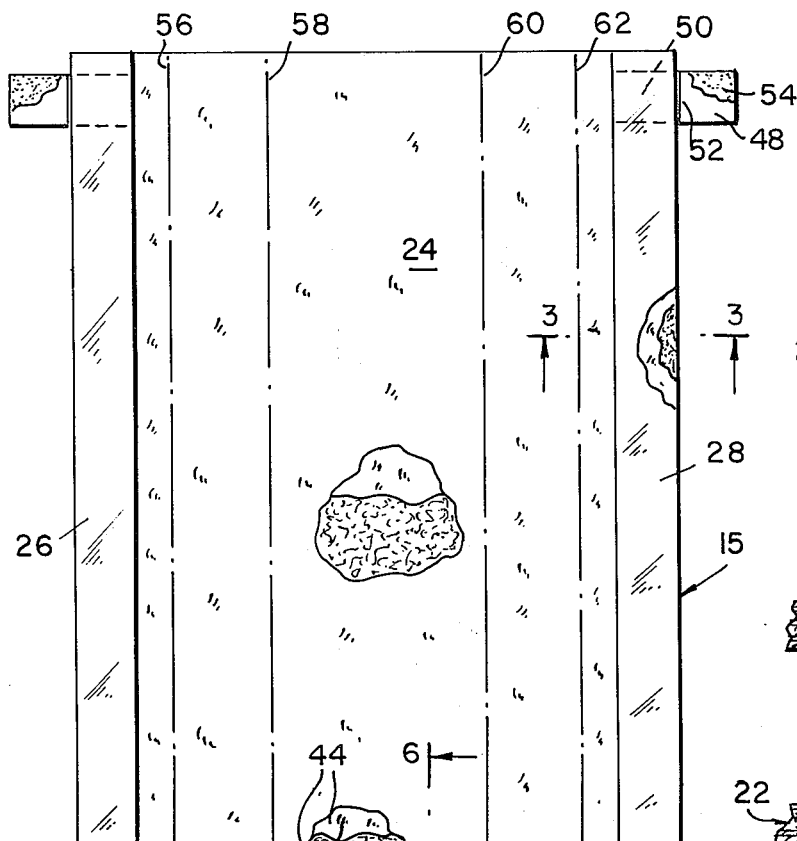
FIG. 1
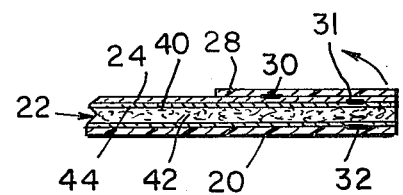
FIG. 3
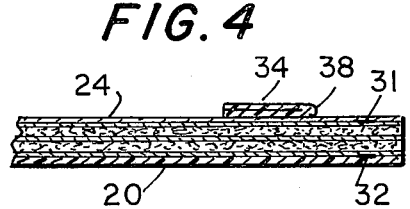
FIG. 4
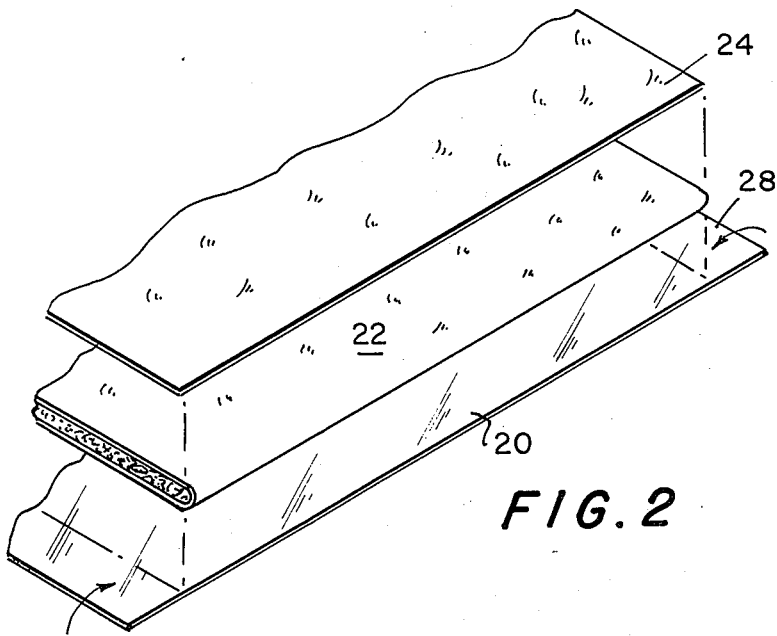
FIG. 2
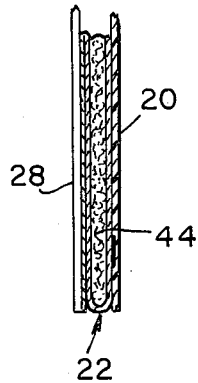
FIG. 5
FIG. 6

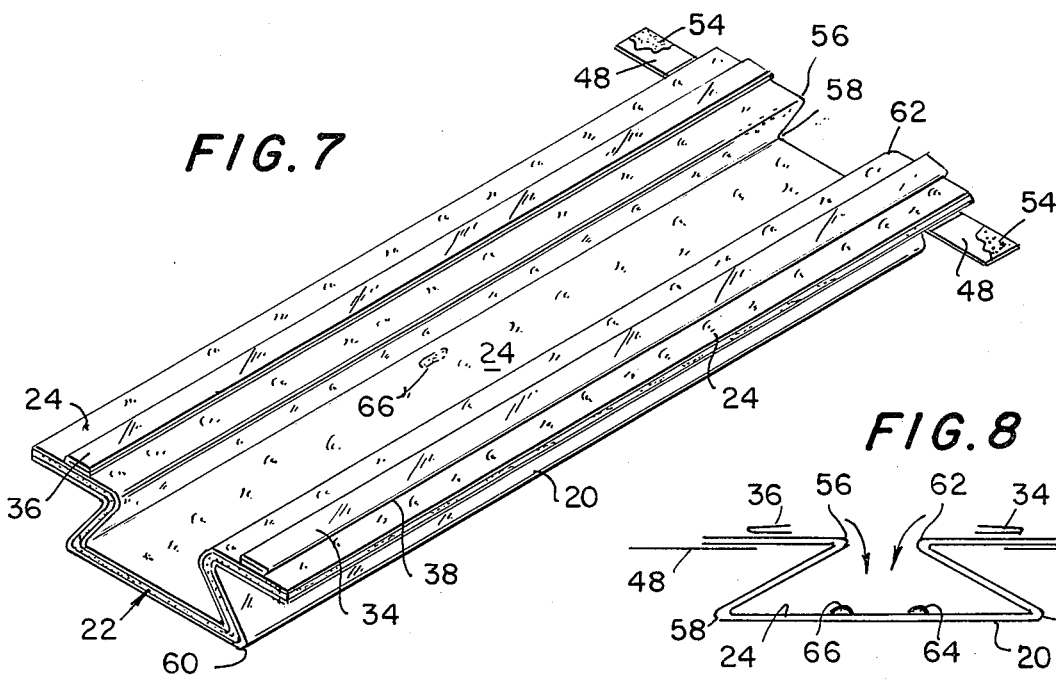
FIG.7
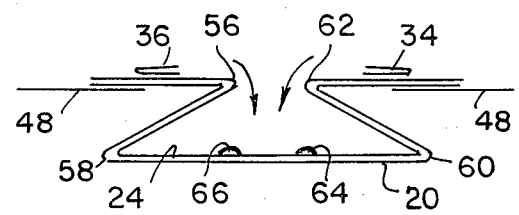
FIG.8
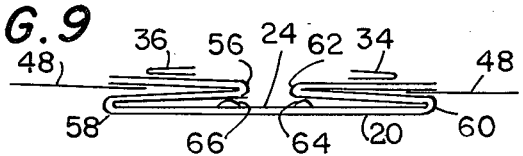
FIG.9
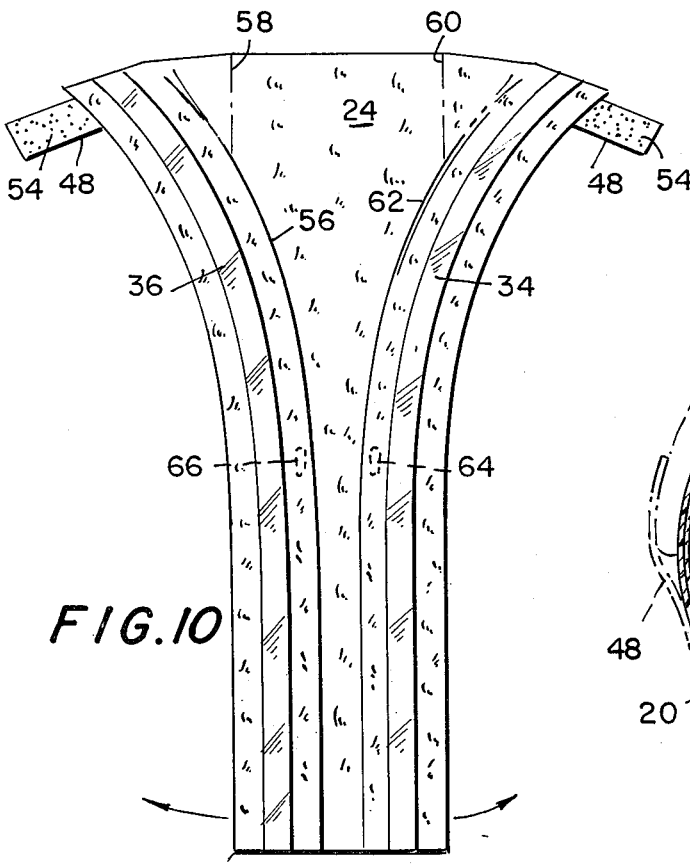
FIG.10
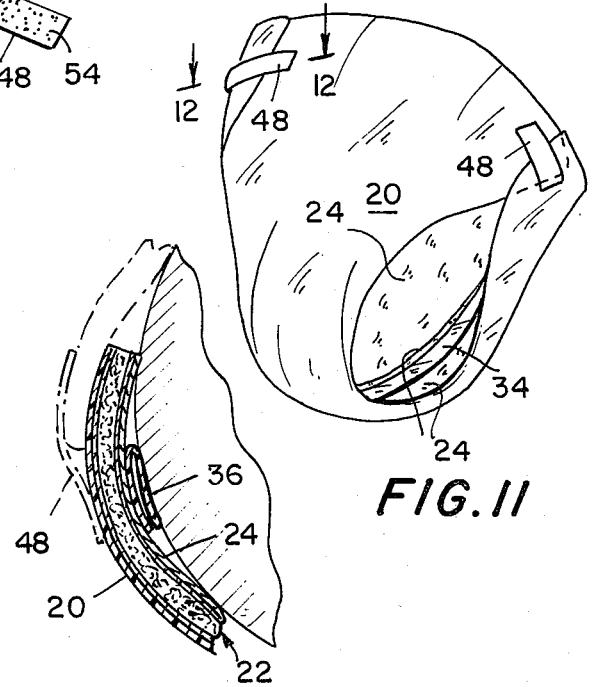
FIG.11
FIG.12

DISPOSABLE DIAPER HAVING FLUID TRAP

BACKGROUND OF THE INVENTION

1. Field of the Invention

This invention relates generally to diapers and more particularly, to an improved disposable diaper having fluid traps along the side edges thereof.

2. DESCRIPTION OF THE PRIOR ART

Conventional disposable diapers comprise a rectangular back sheet of waterproof material, a rectangular absorbent pad and a rectangular top sheet of hydrophobic material. The back sheet is generally wider than the pad and the top or face sheet and the longitudinal edges of the back sheet extend past the longitudinal edges of the pad and the face sheet. The back sheet is folded around the edges of the pad and onto the face sheet forming side flaps. The longitudinal edges of the back sheet are then adhered to the face sheet.

In order to successfully meet consumer expectations a disposable diaper must, as an assembly, have sufficient strength to prevent tearing when applied and when worn by an infant and must also have sufficient limpness or ability to be molded or adjusted by hand to fit closely around the thighs and trunk of an infant. This limpness, or ability to be molded or adjusted by hand, is required in order to create a seal to contain discharged urine in order to give the absorbent pad sufficient time to absorb the urine. Failure to provide these features results in a product which causes soiled clothing, infant discomfort and a general adverse reaction on the part of the consumer.

Present disposable diapers attempt to meet the above goal of having sufficient strength to avoid tearing by providing the above mentioned folded edge of back sheet on each of the longitudinal edges of the diaper. The back sheet on one form of conventional disposable diaper has side flaps which are folded, one each, around the longitudinal edges of the absorbent pad and are fastened to the face sheet by adhesive means. In this form of conventional disposable diaper the combined width of the side flaps are equal to approximately two thirds of the overall width of the diaper in the folded configuration. The side flaps are placed in a complex state of combined bending and tensile stress when the conventional disposable diaper is applied. This results in local buckling and bulging of the back sheet away from the thighs and trunk of the infant with consequent loss of sealing contact.

Another disadvantage of present conventional disposable diapers is that the folding of the back sheet over the edge of the absorbent pad prevents air from contacting the edge of the pad. The consequent thermal insulation of the edges of the pad by the back sheet contributes to the absorbent pad retaining the heat produced by the absorption and accumulation of waste products and also retaining body heat. This heat retaining property of conventional disposable diapers is undesirable since it leads to infant discomfort. In addition to the undesirable effects in conventional disposable diapers related to the side flaps which cover the longitudinal edges of the pad, additional undesireable effects are related to the side flap portions which overlay the face sheet. These portions of the backsheet contribute to the undesirable thermal insulating properties of the conventional disposable diaper. In addition, when the conventional disposable diaper is applied to an infant, the side flap portions which overlay the face sheet form a relatively large portion of the overall width of the diaper in the narrow crotch area. The side flap portions prevent absorption of waste products through the hydrophobic face sheet in those covered areas and actually increase dripping of excess fluid. In addition, in the crotch area, those portions of the back sheet which overlay the face sheet, since they form a relatively large portion of the overall disposable diaper width, readily become wet with urine and cause infant discomfort. In certain cases these wet portions at the edges of the side flaps in contact with the infant's skin can lead to skin rashes and other skin disorders caused by the combined effects of urine and body heat.

A rectangular diaper is disclosed in the U.S. Pat. No. 3,592,194, issued to Robert C. Duncan on July 13, 1971 for DIAPER HAVING IMPROVED WICKING AND DRYNESS. This rectangular diaper is folded in a box pleat such as also disclosed in British Pat. No. 1,011,888 of Dec. 1, 1965.

An object of the invention is to provide a more comfortable and better fitting diaper in which the wicking of fluids is enhanced and a fluid seal is provided.

An additional object of this invention is to provide a disposable diaper having relatively high tensile strength in the longitudinal direction combined with relatively low transverse bending strength.

Another object of this invention is to provide a disposable diaper having increased flexibility of the longitudinal edges or side thereof to facilitate the formation of a desirable tight fit to the leg and trunk of an infant.

A further object of this invention resides in the provision of a disposable diaper having a pair of fluid traps spaced inwardly of the longitudinal edges for increased sealing capability.

SUMMARY OF THE INVENTION

The concept of this invention features an improved disposable diaper having a rectangular waterproof back sheet, an absorbent pad narrower than the back sheet and centered on the back sheet, a hydrophobic face sheet disposed in alignment with the back sheet and on top of the absorbent pad. A pair of longitudinal strips formed by cutting the side flap portions of the back sheet free from the back sheet and made of the same material as the back sheet are disposed, one each, overlying the top sheet. Each of the longitudinal strips has an inwardly directed folded portion extending along the length of the strip to aid in sealing the edge of the disposable diaper. The space along the sides of the diaper therefore expose the hydrophobic sheet to increase absorbent ability of the diaper and thereby reduce chaffing.

These, together with the various ancillary objects and features of this invention, which will become apparent as the following description proceeds are attained by this disposable diaper, preferred embodiments of which are illustrated in the accompanying drawing, by way of example only, wherein:

BRIEF DESCRIPTION OF THE DRAWINGS

FIG. 1 is an overall plan view of a disposable diaper constructed in accordance with the concepts of the present invention prior to being folded;

FIG. 2 is a partial exploded perspective view of the major parts of the disposable diaper;

FIG. 3 is a fragmentary sectional view taken along the plane of the line 3—3 in FIG. 1, in an intermediate state of manufacture;

FIG. 4 is a fragmentary sectional view similar to FIG. 3 in which a longitudinal strip or side flap portion on top of the hydrophobic face sheet is inwardly folded;

FIG. 5 is a sectional detail view similar to FIG. 3 of a modified form of the invention;

FIG. 6 is a fragmentary sectional view taken along the plane of the line 6—6 in FIG. 1;

FIG. 7 is a perspective view of a partially folded disposable diaper constructed in accordance with the embodiment of FIG. 4;

FIG. 8 is a view showing schematically, a partially folded diaper constructed in accordance with the present invention;

FIG. 9 is a schematic view illustrating a completely folded diaper;

FIG. 10 is a top view of the folded diaper of FIG. 4 with one end fanned out in preparation for application to an infant.

FIG. 11 is a perspective view illustrating the configuration of the disposable diaper in use; and FIG. 12 is a fragmentary sectional view taken along the plane of the line 11—11 of FIG. 11.

DESCRIPTION OF THE PREFERRED EMBODIMENTS

With continuing reference to the accompanying drawing, wherein like reference numerals designate similar parts throughout the various views, reference numeral 15 is used to generally designate a disposable diaper constructed in accordance with the concepts of the present invention. The disposable diaper 15 includes a rectangular back or bottom sheet 20 made of a thin flexible plastic material such as polyethylene, polypropylene or polyvinyl chloride. An absorbent pad 22, shorter in width than the bottom sheet 20 is centered on the back sheet 20. A face sheet 24 of hydrophobic material is disposed on top of the absorbent pad 22. The face sheet 24 is of less width than the back sheet 20 and of the same length and is aligned with the back sheet 20. The face sheet 24 may be made of paper or of a non-woven web having the desired properties of softness to touch, porosity and hydrophobic action with respect to fluids. The face sheet 24 is bonded to the back sheet 20 by suitable adhesive about the periphery of the pad 22. The excess width of the back sheet 20 is folded over the face sheet 24 to form side flaps 26 and 28. The use of hydrophobic material permits the passage of fluids from the outside of the disposable diaper 15 through the face sheet 24 and onto the absorbent pad 22 where the fluid is absorbed. The hydrophobic material reduces the area of wetness caused by fluids excreted by an infant as such pass to the absorbent pad 22 through the face sheet 24. As can be seen in FIG. 3, the side flaps 26 and 28 form longitudinal strips which are equal in length to the length of the face sheet 24 and are each approximately equal in width to the distance between the edge of the absorbent pad 22 and the edge of the back sheet 20. The longitudinal strips are entirely severed from the back sheet 20 by a cutting step using cutting blades. The longitudinal strips 26 and 28 are disposed on top of the face sheet 24 and are disposed, one each, between the longitudinal edges of the absorbent pad 22 and the longitudinal edges of the face sheet 24. The longitudinal strips 26 and 28, the top sheet 24, the absorbent pad 22 and the back sheet 20 are held in relative position by means of an adhesive 30 deposited in a narrow line close to the edge of the absorbent pad 22 between the longitudinal strip 26 and the face sheet 24, an adhesive 31 deposited in a narrow line between the absorbent pad 22 and the face sheet 24, and an adhesive 32 deposited in a narrow line between the absorbent pad 22 and the back sheet 20. The adhesive portions 30, 31 and 32 have been described with reference to the longitudinal edge of the disposable diaper on which longitudinal strip 26 is disposed. It is understood that similar adhesive portions are present on the longitudinal edge of the disposable diaper on which longitudinal strip 28 is disposed.

The longitudinal strips 26 and 28 in the embodiment of FIG. 1 is made of the same sheet of thin flexible plastic material as the back sheet 20. In the preferred method of manufacture of the disposable diaper according to the present invention the back or bottom sheet 20 in its original state is larger in width to the bottom sheet in the finished state having as shown in FIG. 1 plus the additional width of the side flaps from which the longitudinal strips 26 and 28 plus a small allowance for cutting or slitting, to be presently explained. In this method of manufacture the back sheet 20 in its original state is deposited as a first step. A pair of narrow adhesive portions are deposited longitudinally on the bottom sheet, with one of such portions shown as adhesive 32 in FIG. 3. Absorbent pad 22 is deposited on top of the back sheet 20 and centered with respect to the longitudinal edges of the back sheet 20. A pair of narrow adhesive portions are deposited on the absorbent pad 22, with one of such portions shown as adhesive 31 in FIG. 3. Top sheet 24 is then deposited on top of the absorbent pad 22 and is centered with respect to the longitudinal edges of the back sheet 20. A pair of narrow adhesive portions are deposited longitudinally on the face sheet 24, with one of such portions shown as adhesive 30 in FIG. 3. Side flaps 26 and 28 of the back sheet 20 are then folded over on to the face sheet 24 and are adhered to the face sheet 24 by means of the narrow adhesive portions deposited on the face sheet 24. The two longitudinal edges of the back sheet 20 which curve around the longitudinal edges of the face sheet are then subjected to a slitting, trimming or cutting operation. This operation cuts longitudinal strips 26 and 28 free of the bottom sheet 20 and the disposable diaper then assumes the configuration shown in FIG. 3.

The slitting or trimming operation which produces the configuration of FIG. 1 and FIG. 3 results in disposable diaper which has longitudinal edges with unexpected flexibility. This is a great advantage in applying the diaper to an infant and results in a neat appearance since the edge can be molded or shaped by hand to fit closely around the legs and trunk of the infant and this close fit helps retain urine and waste matter until it can be absorbed by the absorbent pad. In addition the openings on the longitudinal ends of the disposable diaper according to the present invention between the longitudinal strips, the top sheet, the edge of the pad and the bottom sheet and provide means for absorbing fluid to pad 22 to prevent dripping of excess fluid should such reach the edges of the diaper and also to assure a disposable diaper which is cool and comfortable during use. In the embodiment shown in FIG. 5, the longitudinal strip 26 is formed by the additional cutting action of cutting along the fold 38 as shown in FIG. 4. Alternatively, the back sheet 20 can be made of the same width as the face sheet and the strip 26 separately applied.

The absorbent pad 22 has a porous outer layer 40 or envelope made of a porous paper, or non-woven web and an absorbent inner layer 42 made of cellulose wadding, woodfluff, fiber or the like.

The longitudinal strips 26 and 28 have a portion thereof folded inward toward each other. The fold on longitudinal strip 26 is shown as fold 38 in FIG. 4. A sealing flap 34 is thus formed on longitudinal strip 26 as is shown in FIGS. 4 and 7. A similar sealing flap 36 is formed on longitudinal strip 28 as is shown in FIG. 7. The provision of the sealing flaps 34 and 36 results in several significant advantages. The provision of the sealing flaps 34 and 36 decreases the width of the longitudinal strip which is in contact with the infant's skin. This results in a cooler disposable diaper and a smaller area on the disposable diaper where a waterproof material is in contact with the infant's skin and consequently a smaller area where potential skin rashes and other disorders caused by the continued presence of urine in contact with the skin can occur. The provision of fold 38 on longitudinal strip 28 also increases the number of layers of flexible plastic sheet on the longitudinal edge of the disposable diaper from two layers as shown in FIG. 3 to three layers as shown in FIG. 4. This increase in the number of layers along the longitudinal edges of the disposable diaper is an advantage in the convenient application of the disposable diaper to an infant. In the application of a disposable diaper to an infant significant tension is placed along the longitudinal edges of the diaper in order to make the diaper fit closely around the legs of an infant. It is important to make the edges of the diaper fit closely in order to effect a mechanical seal to enable the diaper to retain urine and waste matter to give the absorbent pad sufficient time to absorb the urine and waste matter. The above mentioned tension is placed on the longitudinal edges by the fingertips which act on a relatively narrow area of the longitudinal strip 28. Although folding the longitudinal strip 28 does not increase the cross-sectional area of the longitudinal strip 28 it however increases the cross-sectional area in the portion of longitudinal strip 28 which is grasped by the hand when the disposable diaper is applied. In other words, the folding of the longitudinal strip 28 into a double thickness narrow strip optimizes the effectiveness of the cross-sectional area of the longitudinal strip 28. In addition, when the disposable diaper 15 in accordance with the present invention is placed on an infant, the sealing flaps 34 and 36 of the longitudinal strips 26 and 28, respectively, tend to flex slightly away from the top sheet 24. This creates two oppositely disposed trough like or channel like portions which act to retain urine and other waste matter.

The longitudinal dimension of the face sheet 24 is approximately equal to the longitudinal dimension of the back sheet 20 and the face sheet 24 is aligned longitudinally with the back sheet 20.

When it is desired to dispose of a soiled diaper in a toilet, the top sheet 24 can be peeled away from the back sheet 20 thus permitting solid waste matter to drop into the toilet and permitting the absorbent pad 22 to drop into the toilet while the waterproof back sheet 20 is held in the hand. The back sheet 20 is then disposed separately and is not flushed down the toilet.

A pair of pressure sensitive tape fasteners 48 are provided on one end of back sheet 20. The fasteners 48 each comprise a strip of pressure sensitive tape divided into a first area 50 in which the tape fastener is adhered to back sheet 20 and a second area in which the tape fastener adhesive film is covered by a release tab 52. Release tabs 52 can be readily peeled away from the adhesive film after the disposable diaper is applied to an infant thus revealing the adhesive film portion 54 and the tape fasteners 48 can be used to secure the ends of the disposable diaper 15 as shown in FIG. 11 and FIG. 12.

The disposable diaper 15 according to the present invention is provided in a pre-folded configuration shown in FIG. 7. This pre-folded configuration is accomplished through the use of longitudinal and parallel folds 56, 58, 60 and 62 shown in FIG. 1. The disposable diaper 15 is folded inwardly along the folds 58 and 60 as is shown in FIG. 7 and FIG. 8 and the disposable diaper 15 is folded outwardly along the folds 56 and 62 as is also shown in FIG. 7 and FIG. 8. The folds 56, 58, 60 and 62 are disposed so that when in the pre-folded condition, shown in FIG. 9, the folds 56 and 62 are spaced. When the disposable diaper 15 is about to be applied to an infant one end is fanned out by gently opening the folds 56, 58, 60 and 62 along approximately one half the length of the disposable diaper 15 as is shown in FIG. 10. Adhesive spots 64 and 66 are provided on the face sheet 24 approximately centered along the length of the disposable diaper 15 and are disposed to adhere the portion of the disposable diaper between the folds 56 and 58 and the portion of the disposable diaper between the folds 60 and 62 each onto the portion of the disposable diaper between the folds 58 and 60. Adhesive spots 64 and 66 assist in unfolding the pre-folded disposable diaper to the configuration shown in FIG. 10. After the disposable diaper 15 is unfolded into the configuration shown in FIG. 10 the infant is placed on the disposable diaper 15 with his buttocks slightly closer to the fanned out end and the unfanned out end is brought up between his legs and also fanned out. The opposite ends of the disposable diaper 15 are then brought together and the tape fasteners 48 are used to secure the ends of the disposable diaper 15 to each other as is shown in FIGS. 11 and 12.

A latitude of modification, substitution and change is intended in the foregoing diclosure and in some instances, some features of the invention will be employed without a corresponding use of other features.

What is claimed is:

1. A disposable diaper comprising a waterproof back sheet, a hydrophobic face sheet, and an absorbent pad sandwiched between said back sheet and said face sheet, said back sheet, said face sheet and said pad being formed into a box pleated configuration in at least the crotch region thereof by means of a plurality of longitudinal folds, and sealing strips of waterproof material separate from a back sheet secured on said face sheet parallel to the side edges thereof in at least the crotch area.

2. A disposable diaper comprising a waterproof back sheet, an absorbent pad overlying said back sheet, and a hydrophobic face sheet overlying said pad, said back sheet, said face sheet and said pad having a plurality of longitudinal folds, said longitudinal folds defining a central panel opposed inwardly extending panels overlying said central panel, and opposed outwardly extending panels overlying said inwardly extending panels, the innermost edges of said inwardly extending panels being in spaced relationship, and sealing strips of waterproof material separate from said back sheet secured to said face sheet parallel to the side edges thereof in at least the crotch area.

3. A disposable diaper comprising a rectangular back sheet, a rectangular absorbent pad disposed on said back sheet, a face sheet disposed on top of said absorbent pad and in alignment with said back sheet, a pair of longitudinal strips separate from said back sheet with a longitudinal edge of each longitudinal strip aligned with a longitudinal edge of said face sheet and with said longitudinal strips disposed on top of said face sheet in at least the crotch area, and adhesive means disposed between adjacent portions of said longitudinal strips and said face sheet, adjacent portions of edges of said face sheet and said absorbent pad and adjacent portions of edges of said pad and said back sheet.

4. A disposable diaper according to claim 3, wherein said back sheet and said longitudinal strips are each made of thin waterproof plastic sheet material.

5. A disposable diaper according to claim 3, wherein said face sheet is made of a hydrophobic paper.

6. A disposable diaper according to claim 3 wherein each of said long strips have a length equal to the length of said back sheet.

7. A disposable diaper according to claim 3, wherein said adhesive means comprises a narrow longitudinal line of adhesive.

8. A disposable diaper according to claim 7, wherein said longitudinal strips each have a longitudinal fold disposed facing said respective longitudinal edge of said face sheet and with said folded portion of said longitudinal strips folded inwardly and disposed on top of the portion of said longitudinal strip adhesively secured to said face sheet.

9. A disposable diaper according to claim 8, wherein said longitudinal fold on said longitudinal strip divides said longitudinal strip into two equal portions.

10. A disposable diaper comprising a waterproof back sheet, a hydrophobic face sheet, and an absorbent pad sandwiched between said back sheet and said face sheet, said back sheet and said pad being formed into a box pleated configuration in at least the crotch region thereof by means of a plurality of longitundinal folds, and sealing strips of waterproof material separate from a said back sheet secured on said face sheet parallel to the side edges thereof in at least the crotch area, said sealing strips each having a longitudinal fold disposed facing the edges of said diaper forming fluid traps.

* * * * *